United States Patent [19]

Brayer et al.

[11] Patent Number: 5,166,167
[45] Date of Patent: Nov. 24, 1992

[54] α-METHYLENE-4-(PHENOXYMETHYL)-5-THIAZOLACETATE

[75] Inventors: Jean-Louis Brayer, Nanteuil Le Haudoin; Jean-Pierre Demoute, Neuilly Plaisance; Gilles Mourioux, Gemenos, all of France

[73] Assignee: Roussel Uclaf, Paris, France

[21] Appl. No.: 851,922

[22] Filed: Mar. 16, 1992

[30] Foreign Application Priority Data

Apr. 10, 1991 [FR] France .................. 91-04340

[51] Int. Cl.$^5$ .................. A01N 43/78; C07D 277/04; C07D 277/30; C07C 69/76
[52] U.S. Cl. ..................... 514/365; 548/187; 548/204; 548/169; 514/369; 560/53
[58] Field of Search ............. 548/187, 204; 514/369, 514/365; 560/53

[56] References Cited

U.S. PATENT DOCUMENTS 4,389,525 6/1983 Bock ................... 548/187

Primary Examiner—Joseph Paul Brust
Assistant Examiner—Robert C. Whittenbaugh
Attorney, Agent, or Firm—Bierman and Muserlian

[57] ABSTRACT

A compound of the formula

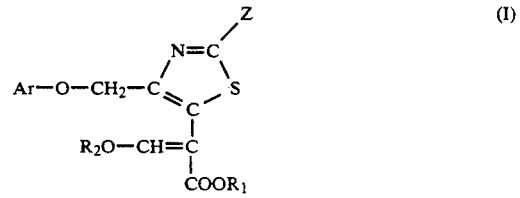

wherein Ar is phenyl optionally substituted with at least one member of the group consisting of halogen, methylenedioxy, phenoxy, phenyl, —CF$_3$ and alkyl, alkoxy and alkylthio of 1 to 6 carbon atoms, Z is selected from the group consisting of hydrogen, chlorine, —CF$_3$ and alkyl, alkoxy and alkylthio of 1 to 6 carbon atoms, R$_1$ and R$_2$ are individually alkyl of 1 to 6 carbon atoms and the exocyclic double bond has (Z) or (E) configuration having fungicidal activity.

13 Claims, No Drawings

α-METHYLENE-4-(PHENOXYMETHYL)-5-THIAZOLACETATE

STATE OF THE ART

Related prior art includes European patent applications No. 0,395,174 and No. 0,402,246 which corresponds to U.S. patent application Ser. No. 533,505 filed June 5, 1990.

OBJECTS OF THE INVENTION

It is an object of the invention to provide the novel compounds of formula I and a process and intermediates for their preparation.

It is another object of the invention to provide novel fungicidal compositions and a novel method of combatting fungi.

These and other objects and advantages of the invention will become obvious from the following detailed description.

THE INVENTION

The novel compounds of the invention have the formula

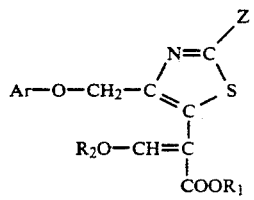

wherein Ar is phenyl optionally substituted with at least one member of the group consisting of halogen, methylenedioxy, phenoxy, phenyl, —$CF_3$ and alkyl, alkoxy and alkylthio of 1 to 6 carbon atoms, Z is selected from the group consisting of hydrogen, chlorine, —$CF_3$ and alkyl, alkoxy and alkylthio of 1 to 6 carbon atoms, $R_1$ and $R_2$ are individually alkyl of 1 to 6 carbon atoms and the exocyclic double bond has (Z) or (E) configuration.

Examples of alkyl of 1 to 6 carbon atoms are methyl, ethyl, propyl, butyl, pentyl or hexyl and in particular methyl, ethyl, propyl, isopropyl, butyl, isobutyl, (R)-sec-butyl, (S)-sec-butyl or tert-butyl. Examples of alkoxy of 1 to 6 carbon atoms are methoxy, ethoxy, propoxy, isopropoxy, butoxy, isobutoxy, (R)-sec-butoxy, (S)-sec-butoxy and tert-butoxy and examples of alkylthio of 1 to 6 carbon atoms are methylthio, ethylthio, propylthio, isopropylthio, butylthio, isobutylthio, (R)-sec-butylthio, (S)-sec-butyl-thio or tert-butylthio.

When Ar is phenyl substituted by one or more halogen atoms, examples are 2-bromo phenyl, 3-bromo phenyl, 4-bromo phenyl-2-chloro phenyl, 3-chloro phenyl, 4-chloro phenyl, 2,6-dichloro phenyl, 2,3,5-trichloro phenyl, 2-fluoro phenyl, 3-fluoro phenyl, 4-fluoro phenyl, 2,3-difluoro phenyl, 2,4-difluoro phenyl, 2,5-difluoro phenyl, 2,6-difluoro phenyl, 3,4-difluoro phenyl, 3,5-difluoro phenyl, 2,3,5,6-tetrafluoro phenyl, 2,3,4,5,6-pentafluoro phenyl, 2-chloro 6-fluoro phenyl or 3-chloro 4-fluoro phenyl.

When Ar is phenyl substituted by one or more alkyl, examples are ortho-, meta- or para-tolyl, 2,4-dimethyl phenyl or mesityl. When Ar is phenyl substituted by one or more alkoxy, examples are 2-methoxy phenyl, 3-methoxy phenyl, 4-methoxy phenyl, 4-ethoxy phenyl, 4-butoxy phenyl, 2,4-dimethoxy phenyl or 3,4,5-trimethoxy phenyl.

When Ar is phenyl substituted by one or more alkylthio, it is preferably 4-methylthio phenyl. When Ar is phenyl substituted by several different substituents, examples are 5-bromo-2-methoxy-phenyl, 3-bromo-4,5-dimethoxy-phenyl, 6-bromo-3,4-dimethoxy-phenyl or 4-methoxy-3-methyl-phenyl.

Among the preferred compounds of formula I are those wherein $R_1$ and $R_2$ are methyl and those wherein Z is hydrogen, chlorine, methyl, ethyl, propyl, isopropyl, methoxy, ethoxy or methylthio. Specific preferred compounds are methyl α-[(Z)-methoxymethylene]-4-phenoxymethyl-5-thiazolacetate and methyl 2-chloro-α-[(Z)-methoxymethylene]-4-phenoxymethyl-5-thiazolacetate.

The novel process of the invention for the preparation of a compound of formula I comprises reacting an ester of 5-halo-4-oxo-pentanoic acid of the formula $$X-CH_2-CO-CH_2-CH_2-COOR_1 \qquad II$$

wherein X is chlorine or bromine and $R_1$ has the above meaning in the presence of a base with a phenol of the formula $$Ar-OH \qquad III$$

wherein Ar has the above meaning to obtain a 5-(aryloxy-4-oxo-pentanoic acid ester of the formula $$Ar-O-CH_2-CO-CH_2-CH_2-COOR_1 \qquad IV$$

reacting the latter with a trialkylchlorosilane of the formula $$R_3R_4R_5SiCl \qquad V$$

wherein $R_3$, $R_4$ and $R_5$ individually are alkyl of 1 to 4 carbon atoms to form a silylated enol ether of the formula $$Ar-O-CH_2-C(OSiR_3R_4R_5)=CH-CH_2-COOR_1 \qquad VI$$

subjecting the latter to bromination to form a 3-bromo derivative of the ester of 5-(aryloxy)-4-oxo pentanoic acid of the formula $$Ar-O-CH_2-CO-CHBr-CH_2COOR_1 \qquad VII$$

reacting the latter either with a product of the formula $$Z_1-CS-NH_2 \qquad VIII$$

wherein $Z_1$ is hydrogen or alkyl of 1 to 6 carbon atoms to form a product of the formula

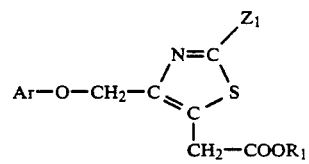

or with a product of the formula $$Alk_1-O-CS-NH_2 \qquad X$$

wherein $Alk_1$ is alkyl of 1 to 4 carbon atoms to form a 2-thiazolinone derivative of the formula

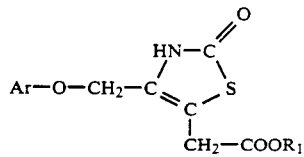 XI reacting the latter with a chlorination reagent of the carbonyl functions to obtain a product of the formula

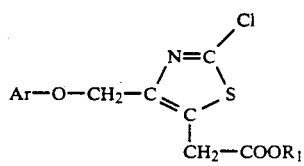 IX$_2$ optionally reacting the product of formula XI with a base of the formula

Z$_3^-$M$^+$  XII wherein Z$_3^-$ is an alcoholate anion and M$^+$ is an ammonium cation or an alkali metal cation to obtain a product of the formula

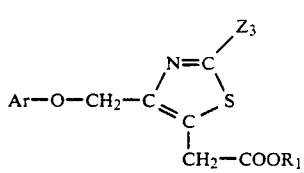 IX$_3$ or with a dithiocarbamate of the formula

NH$_2$—CS—S$^-$M$^+$  XIII to obtain 2-thiazolinethione derivative of the formula

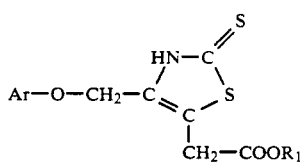 XIV condensing the products of formulae IX$_1$, IX$_2$, IX$_3$ or XIV in the presence of a base with a dimethylformamide acetal of the formula Me$_2$N-CH(OR$_7$)$_2$  XV wherein R$_7$ is alkyl of 1 to 6 carbon atoms to obtain respectively the products of the formulae

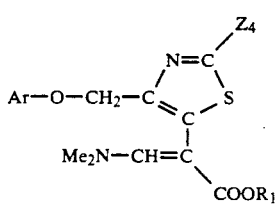 XVI$_1$

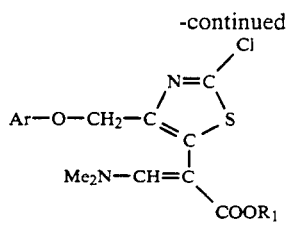 XVI$_2$

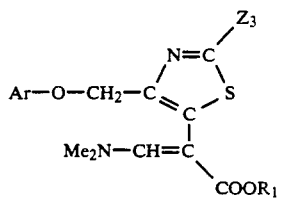 XVI$_3$ and

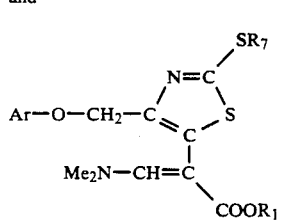 XVI$_4$ which products of formulae XVI$_1$, XVI$_2$, XVI$_3$ and XVI$_4$ can be represented by the single formula

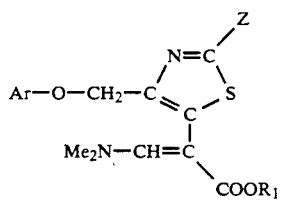 XVI wherein Z, Ar and R$_1$ have the above meanings and converting the latter by hydrolysis into a product of the formula

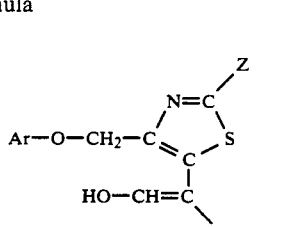 XVII and etherifying the latter into a product of formula I.

In a preferred method of the process, the trialkyl chlorosilane is for example chlorotrimethylsilane or tert-butylchlorodimethylsilane and the reaction is carried out in the presence of a nitrogen base such as 1,5-diaza-5-bicyclo-[5.4.0]-undecene (DBU) or 1,5-diaza-5-bicyclo-[4.3.0]-nonene (DBN). The product of formula VI may be brominated without being purified beforehand by a standard bromination agent such as bromine or N-bromo succinimide (NBS).

The cyclization reaction to form the product of formula IX$_1$ takes place in an alcoholic medium, for example in methanol or ethanol and the preparation of the products of formula XI is carried out by the action of ethyl thiocarbamate on the product of formula VII in methanol or ethanol. The chlorination into the product of formula $IX_2$ is carried out for example by the action of phosphoryl chloride in the presence of a nitrogenous base such as 2,6-lutidine and the alcoholate of formula XII used for obtaining the product of formula $IX_3$ is for example sodium methylate or sodium ethylate.

The dithiocarbamate for the preparation of the product of formula XIV may be ammonium dithiocarbamate and the etherification of the product of formula XVII is carried out with an alkyl halide, for example methyl iodide. The preparation of the products of formula I from the products of formula XVI can be carried out without isolating the intermediate of formula XVII and the preparation of products of formulae $IX_1$, XI and XIV can be carried out without isolating the ester of formula VII.

The starting products of formula II can be prepared from 4-oxo pentanoic acid or levulinic acid which is a commercial product, by esterification of this acid followed by a halogenation in the position of the carbonyl function as in described further on in the preparation of methyl 5-bromo-4-oxo pentanoate. Some products of formula II are known and their preparation is described in: Pichat et al, Bulletin de la Societe Chimique de France (1956), page 1750; Rappe, Ark. Kemi, Volume 14, (1959), pages 467 to 469; Dannenberg et al, Chemisches Bericht, Volume 89, (1956), pages 2242 to 2252; Ratusky et al, Collect. Volume 23, (1958), pages 467 to 476. The products of formula III are commercial products.

The products of formulae VII, $IX_1$, $IX_2$, $IX_3$ XI, XIV, XVI and XVII are new and are also an object of the present invention.

The fungicidal compositions of the invention are comprised of a fungicidally effective amount of at least one compound of formula I and an inert carrier. The compositions may be in the form of powders, granules, suspensions, emulsions, solutions or other preparations usually employed for the use of this type of compound.

Examples of inert carriers are a vehicle and/or an ionic or non-ionic surfactant to ensure an uniform dispersion of the components of the mixture. The vehicle used can be a liquid, such as water, alcohol, hydrocarbons or other organic solvents, a mineral, animal or vegetable oil or a powder such as talc, clays, silicates, kieselghur.

The compositions because of their useful fungicide properties are useful for protection vis-a-vis phathogenic fungi and may be used for protection of plants, protection of premises or the protection of animals as well as in hygiene and human and animal medicine.

The compositions are useful for combating very many phytopathogenic fungi, particularly *Erisyphe graminis, Sphaerotheca macularis, Sphaerotheca fuliginea, Podosphaera leucotricha, Uncinula necator,* Helminthosporium sp., Rhynchosporium sp., *Pseudocercosporella herpotrichoides* and *Gaeumannomyces graminis,* Ustilago sp., *Cercospora arachidicola* and *Cercosporidium personatum*, Cercospora sp., *Botrytis cinerea*, Alternaria sp., *Venturia inaequalis, Plasmopara viticola, Bremia lactucae,* Peronospora sp., *Pseudoperonospora humuli, Pseudoperonospora cubensis, Phytophthora infestans,* Phytophthora sp., *Puccinia recondita, Thanatephorus cucumeris,* Rhizoctonia sp., or also fungi or yeasts affecting human health such as *Candida albicans* or Trychophyton sp.

The novel method of the invention for combatting fungi comprises contacting fungi with a fungicidally effective amount of at least one compound of formula I.

In the following examples, there are described several preferred embodiments to illustrate the invention. However, it should be understood that the invention is not intended to be limited to the specific embodiments.

EXAMPLE 1

Methyl 2-isopropyl-α-[(Z)-methoxy-methylene]-4-(phenoxymethyl)-5-thiazolacetate

STEP A: Methyl (E)-4-oxo-5-phenoxy pentanoate

A solution of 55 g of methyl 5-bromo-4-oxo-pentanoate in 110 ml of acetone was added at 0° to −5° to a solution of 32 g of phenol and 42 g of potassium carbonate in 400 ml of acetone, and the mixture was stirred at this temperature for two hours. The mixture was filtered and the filtrate was concentrated to half its volume, then poured into water and extracted with diethyl ether. The organic phase was dried and filtered and the filtrate was evaporated to dryness. The residue was taken up in methylene chloride, then dried and brought to dryness. After chromatography on silica and eluting with methylene chloride, 30 g of the desired product were obtained. Thin layer chromatography; Rf=0.37 (eluant: methylene chloride).

Infrared Analysis ($CHCl_3$):
non-conjugated ester: 1722 and 1736 $cm^{-1}$;
aromatic ring: 1590, 1599 and 1498 $cm^{-1}$;
NMR Analysis ($CDCl_3$):
O—$CH_3$: 3.67 (s) ppm;
CO—$CH_2$—$CH_2$—CO: 2.65 (t) and 2.90 (t) ppm;
O—$CH_2$—CO: 4.60 (t) ppm;
aromatics protons: 6.89 (d), 6.99 (t) and 7.30 (t) ppm.

STEP B: Methyl 5-phenoxy-4-(trimethylsilyl)-oxo1-3-pentenoate 40 g of the product of Step A, 600 ml of diethyl ether and 27.5 ml of chloro trimethylsilane were mixed together under nitrogen and after the mixture was cooled to 0° C., 32 ml of 1,5-diaza-5-bicyclo-[5.4.0]-undecene (DBU) were added. The mixture was stirred while allowing the temperature to rise to 20° to 25° C. for 90 minutes. After filtration, the ether was evaporated off and the 48 g of the desired product had a boiling point of 138° to 140° C. at 0.05 mm Hg. Thin layer chromatography; Rf=0.5 [eluant: hexane - ethyl acetate (7-3)].

STEP C: Methyl 3-bromo-4-oxo-5-phenoxy pentanoate

A mixture of 6.9 g of the product of Step B and 70 ml of tetrahydrofuran was cooled to 0° C. under nitrogen, and over 10 minutes, 4.6 g of N-bromo succinimide were added. The mixture was stirred for one hour at this temperature and then evaporated to dryness. The residue was taken up in isopropyl ether, filtered and the filtrate was evaporated to dryness under reduced pressure to obtain the brominated derivative which was used as is for the following step.

STEP D: Methyl 2-isopropyl-4-(phenoxymethyl)-5-thiazolacetate

All of the product of Step C was mixed with 50 ml of methanol and 3.1 g of 2-methyl propanethioamide (described in European Patent Application No. 0,402,246) and the mixture was refluxed for two hours, then was poured into water and neutralized by the addition of an aqueous solution of sodium bicarbonate. Extraction was carried out with isopropyl ether and the extracts were dried and evaporated to dryness. The residue was chromatographed on silica, eluting with a hexane - ethyl acetate mixture (7-3) to obtain after evaporation of the solvents, 3 g of the desired product. Thin layer chromatography; Rf=0.15 [eluant: hexane-ethyl acetate (7-3)].

Infrared Analysis:

$CH_3$ of the ester: 1438 cm$^{-1}$;

C=0:1740 cm$^{-1}$; aromatic and heterocyclic ring: 1497, 1588 and 1599 cm$^{-1}$.

NMR Analysis (250 MHz): —CH($CH_3$)$_2$:1.40 (d) ppm; —CH($CH_3$)$_2$:3.30 (m) ppm; —O—($CH_3$): 3.69 (s) ppm; —$CH_2$—CO: 3.90 (s) ppm; —O—$CH_2$: 5.14 (s) ppm; aromatic protons: 6.96 (m) and 7.28 (m) ppm.

STEP E: Methyl -(dimethylamino)-methylene]-2-isopropyl-4-phenoxymethyl)-5-thiazolacetate A mixture of 3 g of the product of Step D and 20 ml of dimethylformamide diethyl acetal was heated to 50° C. and after 16 hours at this temperature, the reaction medium was evaporated to dryness. The residue was chromatographed on silica and eluted with a hexane - ethyl acetate mixture (4-6) to obtain 2.5 g of the desired product which was used as is for the following step. Thin layer chromatography; Rf=0.37 [eluant: hexane - ethyl acetate (4-6)].

STEP F: Methyl α-[(Z)-(hydroxy methylene)1-2-isopropyl-4-(phenoxymethyl)-5-thiazolacetate 2.3 g of the enamine of Step E, 40 ml of tetrahydrofuran, 5 ml of 2N hydrochloric acid and 13 ml of water were mixed together and the mixture was held for 3 hours at 20° to 25° C. The tetrahydrofuran was evaporated off and extraction was carried out with methylene chloride. The extracts were dried and evaporated to dryness under vacuum. The residue was taken up in ether and separated to obtain 1.2 g of the desired product melting at 127.7° C. Thin layer chromatography; Rf=0.20 [eluant: hexane - ethyl acetate (7-3)].

Infrared Analysis:
C=O: 1699 cm$^{-1}$;
C=C: 1640 cm$^{-1}$.

NMR Analysis (250 MHz):
—CH—($CH_3$)$_2$:1.42 (d) ppm;
—CH($CH_3$)$_2$: 3.33 ppm;
—O—($CH_3$) :3.76 (s) ppm;
—O—$CH_2$—:5.01 (s) ppm;
aromatic protons : 6.90 to 7.00 and 7.20 to 7.30 ppm;
=C—H: 7.42 (d,J=13 Hz; s after exchange) ppm;
—O—H: 12.17 (d, J=13 Hz) ppm.

STEP G: Methyl 2-isopropyl-α-[(Z)-methoxy-methylene]-4-(phenoxymethyl)-5-thiazolacetate 4 ml of methyl iodide and 4 g of potassium carbonate were added to a solution of 1.2 g of the product of Step F in 50 ml of acetone and 3 ml of tetrahydrofuran and the mixture was stirred for 3 hours at 20° to 25° C., separated, and evaporated to dryness. The residue was chromatographed on silica and eluted with a hexane - ethyl acetate mixture (7-3) to obtain 1.04 g of the desired product. Thin layer chromatography; Rf=0.30 [eluant: hexane -ethyl acetate (7-3)].

NMR Analysis (CDCl$_3$, 250 MHz):
—CH($CH_3$)$_2$:1.41 (d) ppm;
—CH($CH_3$)$_2$:3.31 (m) ppm;
CO—O—($CH_3$) and C=CH—O—($CH_3$) 3.69 (s) and 3.79 (s) ppm;
—O—$CH_2$—:4.97 (s) ppm;
aromatic protons : 6.88 to 6.95 and 7.20 to 7.30 ppm.
Analysis: $C_{18}H_{21}NO_4S$; molecular weight=347.432:
Calculated: %C,62.23; %H, 6.09; %N,4.03; %S, 9.23,
Found: %C, 62.4; %H, 6.2; %N,4.1; %S, 9.1.

EXAMPLE 2

Methyl α-[(Z)-methoxy-methylene]-2-methyl-4-(phenoxymethyl)-5-thiazolacetate

STEP A: Methyl 2-methyl-4-(phenoxymethyl)-5-thiazolacetate 4.6 g of the product of Step B of Example 1 were mixed with 45 ml of tetrahydrofuran and after the mixture was cooled to 0° C., then 3.1 g of N-bromo succinimide were added. The mixture was stirred for 45 minutes at this temperature and the tetrahydrofuran was evaporated off under reduced pressure. The residue was taken up in isopropyl ether and the crystallized product was filtered and the filtrate was evaporated to dryness. The oily residue was taken up in 30 ml of methanol and 1.5 g of thioacetamide were added. After 2 hours at reflux, the solution was concentrated under vacuum. The residue was dissolved in an aqueous solution of sodium bicarbonate and extraction was carried out with ether. The organic phase was washed with a saturated solution of sodium chloride, dried and evaporated to dryness. The residue was chromatographed on silica and eluted with a hexane - ethyl acetate mixture (75 - 25) to obtain, after evaporation of the solvents, 3.3 g of the desired product. Thin layer chromatography; Rf =0.12 [eluant: hexane -ethyl acetate (75-25)].

NMR Analysis (CDCl$_3$, 250 MHz):
—$CH_3$: 2.68 (s) ppm;
—O—($CH_3$) :3.68 (s) ppm;
—$CH_2$—CO : 3.88 (s) ppm;
—O—$CH_2$: 5.12 (s) ppm;
Aromatic protons: 6.98 (m) and 7.28 (m) ppm.

STEP B: Methyl α-(dimethylamino)-methylene1-2-methyl-4-(phenoxymethyl)-5-thiazolacetate A mixture of 1.6 g of the product of Step A and 20 ml of dimethylformamide diethyl acetal was heated to 50° to 70° C. and after 3 hours at this temperature, the reaction medium was evaporated to dryness. The residue was chromatographed on silica and eluted with a cyclohexane - ethyl acetate mixture (6-4) to obtain 1.3 g of the desired product. Thin layer chromatography; Rf=0.15 [eluant: cyclohexane - ethyl acetate (6-4)].

NMR Analysis (CDCl$_3$, 250 MH):
—$CH_3$: 2.70 (s) ppm;
—N($CH_3$)$_2$: 2.79 (s) ppm;
—O—$CH_3$: 3.63 (s) ppm;
—O—$CH_2$—: 4.91 ppm;
aromatic protons: 6.90 (m) and 7.26 (m) ppm;
=C—H: 7.60 ppm.
Analysis: $C_{17}H_{20}N_2O_3S$; molecular weight=322.421:
Calculated: %C; 61.42, %H,6.06; %N, 8.43; %S, 9.64,
Found: %C, 61.4; %H, 6.1; %N, 8.5; %S, 9.7.

STEP C: Methyl α-[(Z)-(hydroxy-methylene)-1-2-methyl-4-(phenoxy-methyl)-5-thiazolacetate 2.5 g of the enamine of Step B, 40 ml of tetrahydrofuran, 5 ml of 2N hydrochloric acid and 13 ml of water were mixed together and the mixture was held for 4 hours at 20° to 25° C. and neutralized by the addition of sodium bicarbonate. Extraction was carried out with methylene chloride and the organic phase was washed, dried and evaporated to dryness under vacuum. The product was crystallized from ether, separated and dried to obtain 2.15 g of the desired product. Thin layer chromatography; Rf=0 to 0.10 [eluant: cyclohexane - ethyl acetate (6-4)].

NMR Analysis (CDCl$_3$, 250 MHz):
—CH$_3$:2.69 (s) ppm;
—O—(CH$_3$) : 3.76 (s) ppm;
—O—CH$_2$—: 4.97 (s) ppm;
aromatic protons: 6.95 (m) and 7.29 (m) ppm;
=C—H: 7.40 (d, s after exchange);
—O—H: 12.14 (d, mobile) ppm.

STEP D: Methyl α-[(Z)-methoxy methylene]-2-methyl-4-(phenoxy-methyl)-5-thiazolacetate 7 ml of methyl iodide and 3.5 g of potassium carbonate were added to a solution of 2 g of the product of Step C in 70 ml of acetone and the mixture was stirred for 30 minutes at 20° to 25° C. and separated. The filtrate was evaporated to dryness and the residue was chromatographed on silica and eluted with a hexane-ethyl acetate mixture (I-1) to obtain 1.41 g of the desired product. Thin layer chromatography; Rf =0.27 [eluant: hexane-ethyl acetate (1-1)].

NMR Analysis (CDCl$_3$: 250 MHz):
—CH$_3$: 2.70 (s) ppm;
=CH—O: 7.88 (s) ppm;
CO—O—(CH$_3$) and C=CH—O—(CH$_3$) : 3.69 (s) and 3.80 (s) ppm;
—O—CH$_2$:4.95 (s) ppm;
aromatic protons : 6.92 (m) to 7.24 (m) ppm.
Analysis: C$_{18}$H$_{21}$NO$_4$S; molecular weight=319.382;
Calculated: %C, 60.17; %H, 5.36,, %N,4.39; %S, 10.04,
Found: %C, 59.4; %H, 5.3; %N, 4.3; %S, 10.0.

EXAMPLE 3

Methyl α-[(Z)-methoxy methylene]-4-(phenoxymethyl)-5-thiazol-acetate

STEP A: Methyl 4-(phenoxymethyl)-5-thiazolacetate 13.8 g of the product of Step B of Example 1 were mixed with 135 ml of tetrahydrofuran and the mixture was cooled to 0° C. Then, 9.3 g of N-bromo succinimide were introduced, followed by stirring for one hour at this temperature and eliminating the tetrahydrofuran. After taking the product up in isopropyl ether, the crystallized product was filtered and the filtrate was evaporated to dryness. The oily residue was dissolved in 100 ml of methanol and 3.0 g of methanethioamide were added. After two hours at reflux, the mixture was poured into water and neutralized by a saturated aqueous solution of sodium bicarbonate. Extraction was carried out with isopropyl ether and the extracts were washed, dried and evaporated to dryness. The residue was chromatographed on silica, eluting with a hexane - ethyl acetate mixture (7-3) to obtain after evaporation of the solvents, 5 g of the desired product. Thin layer chromatography; Rf=0.2 [eluant: hexane - ethyl acetate (7-3)].

NMR Analysis (CDCl$_3$, 250 MHz):
—O—(CH$_3$) : 3.69 (s) ppm;
—CH$_3$—CO: 3.97 (s) ppm;
—O—CH$_2$—:5.23 (s) ppm;
aromatic protons : 6.96 (m) and 7.28 (m) ppm;
N=C—H :8.70 (s) ppm.

STEP B: Methyl α-[(dimethylamino)-methylene1-4-(phenoxy-methyl)-5-thiazolacetate A mixture of 5 g of the product of Step A and 30 ml of dimethylformamide diethyl acetal was heated for 2 hours at 50° C. and then evaporated to dryness. The residue was chromatographed on silica, eluting with a hexane - ethyl acetate mixture (4-6) to obtain 3 g of the desired product which was used as is for the following step. Thin layer chromatography; Rf =0.3 [eluant: hexane - ethyl acetate (4-6)].

STEP C: Methyl α-(Z)-(hydroxy-methylene)]-4-(phenoxymethyl)-5-thiazolacetate 3 g of the enamine of Step B, 50 ml of tetrahydrofuran, 5 ml of 2N hydrochloric acid and 15 ml of water were mixed together and the mixture stood for 2 hours 30 minutes at 20° to 25° C. The tetrahydrofuran was evaporated and extraction was carried out with methylene chloride. The organic phase was washed, dried and evaporated to dryness under vacuum. The residue was crystallized from isopropyl ether, separated and dried to obtain 2.5 g of the desired product melting at 133° C. Thin layer chromatography; Rf=0.25 [eluant: hexane - ethyl (7-3)].

NMR Analysis (DMSO, 250 MHz):
—O—(CH$_3$) :3.61 (s) ppm;
—O—CH$_2$—: 4.96 (s) ppm;
aromatic protons : 6.90 (m) and 7.25 (m) ppm;
=C—H : 7.98 (s) ppm;
N=C—H : 9.06 (s) ppm;
—O—H: 11.77 (mobile) ppm.

STEP D: Methyl α-(Z)-methoxy-methylene1-4-(phenoxymethyl)-5-thiazolacetate 8 ml of methal iodide and 4 g of potassium carbonate were added to a solution of 2.5 g of the product of Step C in 100 ml of acetone and 20 ml of tetrahydrofuran and the mixture was stirred for 4 hours at 20° to 25° C. and filtered. The filtrate was evaporated to dryness and the residue was chromatographed on silica, eluting with a hexane - ethyl acetate mixture (4-6) to obtain 1.7 g of the desired product. Thin layer chromatography; Rf=0.35 [eluant: hexane - ethyl acetate (4-6)].

NMR Analysis (250 NMz):
CO—O—(CH$_3$) and C=CH—O—(CH$_3$) :3.69 (s) and 3.81 (s) ppm;
—O—CH$_2$—: 5.07 (s) ppm;
aromatic protons : 6.88 to 6.96 and 7.19 to 7.27 ppm;
C=C—H : 7.62 (s) ppm;
N=C—H : 8.82 (s) ppm.
Analysis: C$_{15}$H$_{15}$NO$_4$S; molecular weight=305.356:
Calculated: %C,59.00, %H, %H, 4.95; %N, 4.59; %S, 10.5,
Found: %C, 58.5; %H, 4.9; %N, 4.5; %S, 10.5.

EXAMPLE 4

Methyl 2-chloro-α-[(Z)-methoxy-methylene1-4-(phenoxymethyl)-5-thiazolacetate

STEP A: Methyl 2.3-dihydro-2-oxo-4-(phenoxymethyl)-5-thiazol-acetate 18 g of the product of Step B of Example 1 were mixed with 180 ml of tetrahydrofuran, and the mixture was cooled to 0°/+5° C. Then, 12 g of N-bromo succinimide were added and stirring was carried out for one hour, followed by evaporation to dryness. The residue was taken up in isopropyl ether, the mixture was filtered and the filtrate was evaporated to dryness under vacuum. The oil was taken up in 150 ml of methanol and then 7 g of ethyl thiocarbamate were added, followed by reflux for 3 hours. The mixture was poured into water and extracted with methylene chloride. The extracts were dried and evaporated to dryness to obtain after crystallization from isopropyl ether, 8.3 g of the desired product melting at 103° C. Thin layer chromatography; Rf=0.42 [eluant: hexane - ethyl acetate (1-1)].

NMR Analysis (250 MHz) ppm:
—$CO_2$—$CH_3$: 3.72 (s);
—CO—$CH_2$: 3.53 (s);
O—$CH_2$: 4.79 (s);
NH: 9.80 (mobile);
Aromatics: 6.90 to 7.05 (s) and 7.25 to 7.35 (m).

STEP B: Methyl 2-chloro-4-(phenoxymethyl)-5-thiazolacetate 12 g of the product of Step A were mixed with 24 ml of phosphoryl chloride. and then 5 ml of 2,6-lutidine were introduced drop-wise. After reflux for 3 hours, the mixture was allowed to return to 20° to 25° C. The excess phosphoryl chloride was removed under reduced pressure and the reaction medium was poured into 80 ml of ice-cooled water. Extraction was carried out with methylene chloride and the organic phase was washed, dried and evaporated to dryness. The residue was chromatographed on silica, eluting with a hexane - ethyl acetate mixture (7-3) to obtain after evaporation of the solvents, 9 g of the desired product. Thin layer chromatography; Rf=0.32 [eluant: hexane - ethyl acetate (7-3)].

IR Spectrum:
C=O: 1740 cm$^{-1}$;
Aromatic+: 1598–1590;
conjugated system : 1496–1488 cm$^{-1}$;

STEP C: Methyl 2-chloro-α-[(dimethylamino)-methylene1-4-(phenoxymethyl)-5-thiazolacetate A mixture of 4 g of the product of Step B and 50 ml of dimethylformamide diethyl acetal was heated at 50° C. for 3 hours and then was evaporated to dryness. The residue was chromatographed on silica, eluting with a hexane - ethyl acetate mixture (7-3) to obtain 1.5 g of the desired product melting at 113.8° C. Thin layer chromatography; Rf=0.25 [eluant: hexane - ethyl acetate (7-3)].

STEP D: Methyl 2-chloro-α-[hydroxy-methylene]-4-(phenoxy-methyl)-5-thiazolacetate 2.2 g of the product of Step C were mixed with 50 ml of tetrahydrofuran and then 4 ml of 2N hydrochloric acid and 10 ml of water were added. The mixture stood at 20° to 25° C. for 2 hours and then the solvent was evaporated under reduced pressure. The residue was extracted with methylene chloride and the organic phase was dried and evaporated to dryness to obtain 2.1 g of the desired product. Thin layer chromatography; Rf=0.1 to 0.3 [eluant: hexane - ethyl acetate (7-3)].

IR Spectrum:
C=O: 1664 cm$^{-1}$ chelated ester;
C=C+: 1599–1590;
Aromatic+: 1544–1496 cm$^{-1}$;
Heterocycle.

STEP E: Methyl 2-chloro-α-[(Z)-methoxy-methylene1-4-(phenoxy-methyl)-5-thiazolacetate 8 ml of methyl iodide and 4 g of potassium carbonate were added to a solution of 2 g of the product of Step D in 50 ml of acetone and the mixture was stirred for 4 hours. 30 minutes at 20° to 25° C. After neutralization with an aqueous solution of N hydrochloric acid, the medium was extracted with methylene chloride. The organic phase was washed, dried and evaporated to dryness. The residue was chromatographed on silica, eluting with a hexane-ethyl acetate mixture (7-3) to obtain after evaporation of the solvents, 1.5 g of the desired product. Thin layer chromatography; Rf=0.25 [eluant: hexane - ethyl acetate (6-4)].

NMR Analysis:
CO—O—($CH_3$) and C=CH—O—($C_3$) 3.70 (s) and 3.82 (s) ppm;
—O—$CH_2$—: 4.95 (s) ppm;
aromatic protons : 6.8 to 7.0 (m) and 7.2 to 7.4 (m) ppm;
C=C—H : 7.58 (s) ppm.

Analysis: $C_{15}H_{14}ClNO_4S$; molecular weight=334.796;
Calculated: %C, 53.02; %H, 4.15; %Cl, 10.43; %N, 4.12; %S, 9.45.
Found: %C, 52.9, %H, 4.1; %Cl, 10.6; %N,4.1; %S, 9.5.

EXAMPLE 5

Methyl α-[(Z)-methoxy methylene1-2-methylthio-4-(phenoxymethyl)-5-thiazolaoetate

STEP A: Methyl 4-(phenoxymethyl)-2-thioxo-5-thiazolacetate 6 g of N-bromo succinimide were added to a solution of 9 g of the product of Step B of Example 1 in 90 ml of tetrahydrofuran cooled to 0° C. and the mixture was stirred for one hour at this temperature. After evaporation to dryness, the residue was taken up in isopropyl ether and the succinimide was separated off. Then, the filtrate was evaporated to dryness and the oil obtained was dissolved in 70 ml of methanol, then treated with 3.5 g of ammonium dithiocarbamate for one hour at reflux. The mixture was poured into water and the product was separated out, taken up in methylene chloride, dried and evaporated to dryness under vacuum. After crystallization from isopropyl ether, 3.6 g of the desired product melting at 137.8° C. were obtained. Thin layer chromatography; Rf= 0.40 [eluant: methylene chloride - ethyl acetate (9-1)].

IR Spectrum:
C=NH : 3385 cm$^{-1}$;
$CO_2$—$CH_3$: 174–1438 cm$^{-1}$;
C=C : 1625 cm$^{-1}$.

STEP B: Methyl α-(dimethylamino)-methylene]-4-methylthio-4-(phenoxymethyl)-5-thiazolacetate A mixture of 3.4 g of the product of Step A and 25 ml of dimethylformamide diethyl acetal was heated at 50° C. for 2 hours and then evaporated to dryness. The residue was chromatographed on silica, eluting with a hexane - ethyl acetate mixture (6-4) to obtain 2.1 g of the desired product melting at 122.1° C. Thin layer chromatography; Rf=0.22 [eluant: hexane - ethyl acetate (6-4)].

STEP C: Methyl α-[hydroxy-methylene]-4-methylthio-4-(phenoxymethyl)-5-thiazolacetate 2.1 g of the product of Step B were mixed with 45 ml of tetrahydrofuran and then 3.4 ml of 2N hydrochloric acid were added. The mixture stood at 20° to 25° C. for 16 hours. The solvent was evaporated under vacuum, and the medium was extracted with methylene chloride. The organic phase was dried and evaporated to dryness to obtain 1.89 g of the desired product. Thin layer chromatography; Rf=0.25 [eluant: hexane - ethyl acetate (4-6)].

IR Spectrum:
C=O : 1701-1666 cm$^{-1}$;
C=C+: 1635-1618;
Aromatic+: 1598-1590;
Heterocycle: 1548-1497 cm$^{-1}$;

STEP D: Methyl α-[(Z-methoxy-methylene]-4-methylthio-4-(phenoxymethyl)-5-thiazolacetate 1.8 g of the product of Step C were dissolved in 70 ml of acetone, and the solution was treated with 7 ml of methyl iodide and 4 g of potassium carbonate with stirring for 75 minutes at 20° to 25° C. The mixture was poured into water and neutralized by the addition of 2N hydrochloric acid. Extraction was carried out with methylene chloride and the organic phase was washed, dried and evaporated to dryness. The residue was chromatographed on silica, eluting with a hexane - ethyl acetate mixture (7-3) after evaporation of the solvents to obtain 1.56 g of the desired product. Thin layer chromatography; Rf=0.25 [eluant: hexane - ethyl acetate (7-3)].

NMR Analysis (CDCl$_3$250 MHz):
S—CH$_3$: 2.66 (s);
CO—O—(CH$_3$) and C=CH—O—(CH$_3$) : 3.68 (s) and 3.79 (s) ppm; —O—CH$_2$—: 4.96 (s) ppm;
aromatic protons: 6.9 to 6.93 and 7.19 to 7.27 ppm;
C=C—H : 7.56 (s) ppm.

Analysis: C$_{16}$H$_{17}$NO$_4$S$_2$; molecular weight=351.438:
Calculated: %C,54.68., %H,4.88; % N, 3.99; %S, 18.24,
Found: %C, 54.6; %H, 4.8; %N, 4.1; %S, 18.1.

Preparation of methyl 5-bromo-4-oxo pentanoate

STEP A: Methyl 4-oxo-pentanoate

A solution of 300 g of 4-oxo pentanoic acid (levulinic acid), 300 ml of methanol and 2 ml of 97% sulfuric acid was stirred for 16 hours at 20° to 25° C. and then evaporated to dryness. The residue was recitified under reduced pressure to obtain 290 g of the expected methyl ester with a boiling point of 87° to 88° C. at 16 mm Hg. Thin layer chromatography; Rf=0.13 [eluant: hexane-ethyl acetate (8-2)].

STEP B: Methyl 5-bromo-4-oxo pentanoate 100 g of the ester of Step A were mixed with 1600 ml of methanol and 2 ml of concentrated acetic acid and the mixture was heated to 40° C. Then, 42 ml of bromine were introduced and the temperature was allowed to return to 25° C. with stirring. The mixture was evaporated to dryness and the residue was dissolved in 100 ml of water and neutralized with a saturated aqueous solution of sodium bicarbonate. After extraction with diethyl ether, the organic phase was dried over magnesium sulfate, filtered and evaporated to dryness. The residue was chromatographed on silica to obtain the desired product with a yield of 34%. Thin layer chromatography: Rf=0.18 [eluant: hexane - ethyl acetate (8-2)].

BIOLOGICAL STUDY

Study of the Fungicide Activity

Tests on Puccinia *recondita tritici*

Wheat seeds (Festival variety) were germinated in an earth/compost/sand mixture (⅓, ⅓, ⅓) and the plants were cultivated in a greenhouse. The products were dissolved in "matrix A" just before the test at a concentration of 500 ppm. The treatment was carried out by spraying the product solution on the 9-day old wheat plants, until maximum retention was achieved. The contamination by Puccinia recondita tritici uredospores was carried out the day after treatment. The plants were kept in an air-conditioned room (daytime temperature: 22° C., night-time temperature: 18° C.). 7 days after the contamination, the density of spores was measured on the first two leaves of each plant. The effectiveness of the product was calculated relative to a non-treated control.

| Results: | |
|---|---|
| EX. | Test |
| 3 | 100% |
| 4 | 80% |

| Example of compositions. | |
|---|---|
| Matrix A: | |
| SOLVESSO 150 | 70.0 g |
| NAPSOL PM1 | 850.0 g |
| SURFAROX HRH 40C | 52.0 g |
| ECD 1604 | 28.0 g |
| | 1000.0 g |

Various modifications of the products and method of the invention may be made without departing from the spirit or scope thereof and it is to be understood that the invention is intended to be limited only as defined in the appended claims.

What we claim is:

1. A compound of the formula $$\text{Ar—O—CH}_2\text{—C} \begin{array}{c} \text{N=C} \\ \diagup \quad \diagdown \\ \text{C} \quad \text{S} \\ | \\ \text{R}_2\text{O—CH=C} \\ | \\ \text{COOR}_1 \end{array} \quad \text{Z} \quad (I)$$

wherein Ar is phenyl optionally substituted with at least one member of the group consisting of halogen, methylenedioxy, phenoxy, phenyl, —CF₃ and alkyl, alkoxy and alkylthio of 1 to 6 carbon atoms, Z is selected from the group consisting of hydrogen, chlorine, —CF₃ and alkyl, alkoxy and alkylthio of 1 to 6 carbon atoms, $R_1$ and $R_2$ are individually alkyl of 1 to 6 carbon atoms and the exocyclic double bond has (Z) or (E) configuration.

2. A compound of claim 1 wherein $R_1$ and $R_2$ are methyl.

3. A compound of claim 1 wherein Z is selected from the group consisting of hydrogen, chlorine, methyl, ethyl, propyl, isopropyl, methoxy, ethoxy and methylthio.

4. The compounds of claim 1 which are methyl α-[(Z)-methoxy-methylene-4-phenoxymethyl-5-thiazolacetate and methyl 2-chloro-α-[(Z) methoxymethylene]-4-(phenoxymethyl)-5-thiazolacetate.

5. A fungicidal composition comprising a fungicidally effective amount of at least one compound of claim 1 and an inert carrier.

6. A composition of claim 5 wherein $R_1$ and $R_2$ are methyl.

7. A composition of claim 5 wherein Z is selected from the group consisting of hydrogen, chlorine, methyl, ethyl, propyl, isopropyl, methoxy, ethoxy and methylthio.

8. A composition of claim 5 wherein the compounds are methyl α-[(Z)-methoxymethylene]-4-(phenoxymethyl)-5-thiazolacetate and methyl 2-chloro-α-[(Z)-methoxymethylene]-4-(phenoxymethyl)-5-thiazolacetate.

9. A method of combatting fungi comprising contacting fungi with a fungicidally effective amount of at least one compound of claim 1.

10. A method of claim 9 wherein $R_1$ and $R_2$ are methyl.

11. A method of claim 9 wherein Z is selected from the group consisting of hydrogen, chlorine, methyl, ethyl, propyl, isopropyl, methoxy, ethoxy and methylthio.

12. A method of claim 9 wherein the compounds are methyl-α-[(Z)-methoxymethylene]-4-(phenoxymethyl)-5-thiazolacetate and methyl 2-chloro-α-[(Z)-methoxymethylene]-4-(phenoxymethyl)-5-thiazolacetate.

13. A compound having a formula selected from the group consisting of Ar—O—CH₂—CO—CHBr—CH₂COOR₁ VII

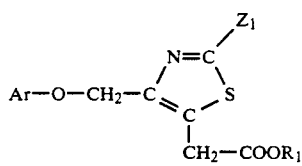

IX₁

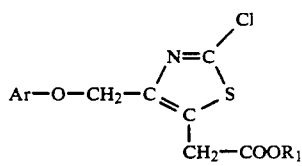

IX₂

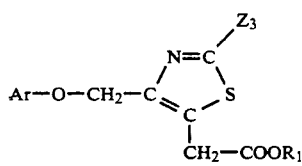

IX₃

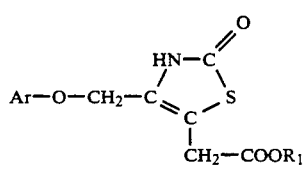

XI

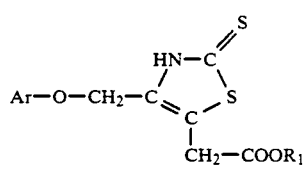

XIV

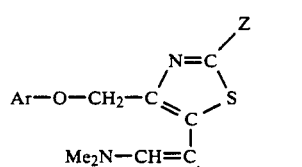

XVI and

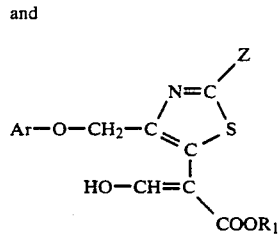

XVII wherein Ar, $R_1$ and Z have the definition of claims 1, $Z_1$ is hydrogen or alkyl of 1 to 6 carbon atoms and $Z_3$ is alkoxy of 1 to 6 carbon atoms.

* * * * *